US008561606B2

(12) United States Patent
Korneff

(10) Patent No.: US 8,561,606 B2
(45) Date of Patent: Oct. 22, 2013

(54) HEAT AND MOISTURE EXCHANGE UNIT

(75) Inventor: Neil Alex Korneff, Diamond Bar, CA (US)

(73) Assignee: CareFusion 2200, Inc., San Diego, CA (US)

( * ) Notice: Subject to any disclaimer, the term of this patent is extended or adjusted under 35 U.S.C. 154(b) by 856 days.

(21) Appl. No.: 12/133,929

(22) Filed: Jun. 5, 2008

(65) Prior Publication Data
US 2009/0301475 A1 Dec. 10, 2009

(51) Int. Cl.
*A61M 5/24* (2006.01)

(52) U.S. Cl.
USPC ............. 128/201.13; 128/203.15; 128/203.26

(58) Field of Classification Search
USPC ............. 128/201.13, 203.12, 200.24, 200.14, 128/201.25, 203.15, 20.316, 203.26, 205.27
See application file for complete search history.

(56) References Cited

U.S. PATENT DOCUMENTS

| | | |
|---|---|---|
| 3,731,678 A | 5/1973 | Pyzel |
| 3,747,598 A | 7/1973 | Cowans |
| 3,881,482 A | 5/1975 | Lindholm |
| 4,061,698 A | 12/1977 | Thornwald |
| 4,090,513 A | 5/1978 | Togawa |
| 4,177,945 A | 12/1979 | Schwartz et al. |
| 4,318,398 A | 3/1982 | Oetjen et al. |
| 4,699,136 A | 10/1987 | Krauser |
| 4,805,609 A | 2/1989 | Roberts et al. |
| 4,825,863 A | 5/1989 | Dittmar et al. |
| 4,951,659 A | 8/1990 | Weiler et al. |
| 5,383,447 A | 1/1995 | Lang |
| 5,460,172 A * | 10/1995 | Eckerbom et al. ........ 128/201.13 |
| 5,468,451 A * | 11/1995 | Gedeon .......................... 422/416 |
| 5,482,031 A | 1/1996 | Lambert |
| 5,505,768 A | 4/1996 | Altadonna |
| 5,546,930 A | 8/1996 | Wikefeldt |
| 5,590,644 A | 1/1997 | Rosenkoetter |

(Continued)

FOREIGN PATENT DOCUMENTS

| | | |
|---|---|---|
| DE | 3928530 | 6/1990 |
| DE | 20 2004 008 959 U1 | 9/2004 |

(Continued)

OTHER PUBLICATIONS

M. Shelly et al., "A Comparison of Five Heat and Moisture Exchangers;" Anaesthesia, vol. 41, 1986, pp. 527-532.

(Continued)

*Primary Examiner* — Elizabeth Houston
*Assistant Examiner* — Bradley Philips
(74) *Attorney, Agent, or Firm* — McDermott Will & Emery LLP

(57) ABSTRACT

A heat and moisture exchange unit for use with a patient breathing circuit. The unit includes a housing, an MDI port assembly and a heat and moisturizing medium. The housing forms a patient-side port, a ventilator-side port, and a containment region between the patient-side port and the ventilator-side port. The MDI port assembly includes a frame projecting into the containment region and configured to receive a portion of a metered dose dispenser. The frame terminates at an outlet end, forming a flow passage. The heat and moisturizing medium is maintained within the containment region so as to define a medium face most proximate the outlet end of the MDI port assembly. The unit is characterized by the absence of a body between the outlet end and the medium face.

18 Claims, 5 Drawing Sheets

(56) References Cited

U.S. PATENT DOCUMENTS

| | | |
|---|---|---|
| 5,605,149 A | 2/1997 | Warters |
| 5,690,099 A | 11/1997 | Abramov et al. |
| 5,701,891 A | 12/1997 | Groenke |
| 5,727,616 A | 3/1998 | Groenke |
| 5,829,428 A | 11/1998 | Walters et al. |
| 5,992,413 A * | 11/1999 | Martin et al. ............ 128/201.13 |
| 6,014,972 A * | 1/2000 | Sladek .................... 128/203.12 |
| 6,095,135 A | 8/2000 | Clawson et al. |
| 6,103,181 A | 8/2000 | Berger |
| 6,105,576 A | 8/2000 | Clawson et al. |
| 6,155,252 A | 12/2000 | Warters |
| 6,269,813 B1 | 8/2001 | Fitzgerald et al. |
| 6,330,883 B1 | 12/2001 | Berger |
| 6,363,930 B1 * | 4/2002 | Clawson et al. ......... 128/201.13 |
| 6,415,788 B1 | 7/2002 | Clawson et al. |
| 6,478,026 B1 | 11/2002 | Wood |
| 6,550,476 B1 | 4/2003 | Ryder |
| 6,588,421 B1 | 7/2003 | Diehl et al. |
| 6,588,427 B1 | 7/2003 | Carlsen et al. |
| 6,745,766 B2 | 6/2004 | Fini |
| 6,769,430 B1 | 8/2004 | Carlsen et al. |
| 6,792,430 B1 | 9/2004 | Kenyon et al. |
| 6,792,946 B1 | 9/2004 | Waldo, Jr. et al. |
| 6,918,389 B2 | 7/2005 | Seakins et al. |
| 6,951,216 B2 | 10/2005 | Heinonen |
| 6,968,841 B2 | 11/2005 | Fini |
| 6,976,488 B2 | 12/2005 | Halperin |
| 7,069,928 B1 | 7/2006 | Waldo, Jr. et al. |
| 7,146,979 B2 | 12/2006 | Seakins et al. |
| 2004/0084046 A1 | 5/2004 | Halperin |
| 2004/0118402 A1 | 6/2004 | Heinonen |
| 2004/0123974 A1 | 7/2004 | Marler et al. |
| 2004/0255952 A1 | 12/2004 | Carlsen et al. |
| 2005/0139211 A1 | 6/2005 | Alston et al. |
| 2005/0178381 A1 | 8/2005 | Daugherty |
| 2005/0252509 A1 | 11/2005 | Rustad et al. |
| 2006/0157056 A1 | 7/2006 | Burk |
| 2006/0219243 A1 | 10/2006 | Walstrom |
| 2006/0283447 A1 | 12/2006 | Dhuper et al. |
| 2007/0267010 A1 | 11/2007 | Fink et al. |

FOREIGN PATENT DOCUMENTS

| | | |
|---|---|---|
| DE | 10 2005 007 234 B3 | 7/2006 |
| EP | 0 730 878 A2 | 9/1996 |
| EP | 1 068 889 A1 | 7/1999 |
| EP | 1 192 968 B1 | 11/2004 |
| JP | 10235126 | 9/1998 |
| WO | 90/10775 | 9/1990 |
| WO | 00/02609 | 1/2000 |
| WO | 02/26306 | 4/2002 |
| WO | 2005/047797 A2 | 5/2005 |
| WO | 2005/058403 A1 | 6/2005 |
| WO | 2005/078667 A1 | 7/2006 |
| WO | 2006/127257 A2 | 11/2006 |

OTHER PUBLICATIONS

I.L. Cohen et al., "Endotrachaeal Tube Occlusion Associated with the Use of Heat and Moisture . . . ;" Critical Care Med, 1988, pp. 277-279.
Sims, Inc., "Filters and Heat & Moisture Exchangers;" Sims, Inc., 1997, pp. 1-8.
Pall Biomedical Products Corp., "The Pall Corporation Heat and Moisture Exchanger;" Pall Biomed, 1985, pp. 1-8.
A PCT Search Report (mailed Aug. 19, 2009); 19 pgs.
European Office Action (EP 0 759 446.9) dated Jul. 26, 2011 (4 pages).

\* cited by examiner

HEAT AND MOISTURE EXCHANGE UNIT

FIELD

The present disclosure relates generally to components for a patient breathing circuit. More particularly, the present disclosure relates to a heat and moisture exchange ("HME") unit useful with a patient breathing circuit.

BACKGROUND

The use of ventilators and breathing circuits to assist in patient breathing is well known in the art. The ventilator and breathing circuit provides mechanical assistance to patients who are having difficulty breathing on their own. During surgery and other medical procedures, the patient is often connected to a ventilator to provide respiratory gases to the patient. One disadvantage of such breathing circuits is that the delivered air does not have a humidity level and/or temperature appropriate for the patient's lungs.

To provide air with desired humidity and/or temperature to the patient, an HME unit can be fluidly connected to the breathing circuit. As a point of reference, HME is a generic term, and can include simple condenser humidifiers, hygroscopic condenser humidifiers, hydrophobic condenser humidifiers, etc.

In general terms, HME units consist of a housing that contains a layer of heat and moisture retaining media or material ("HM media"). The HM media has the capacity to retain moisture and heat from the air that is exhaled from the patient's lungs, and then transfer the captured moisture and heat to the ventilator-provided air of the inhaled breath. The HM media can be formed of foam, paper or other suitable materials that are untreated or treated, for example, with hygroscopic material.

While the HME unit addresses the heat and humidity concerns associated with ventilator-provided air in the breathing circuit, other drawbacks may exist. For example, it is fairly common to introduce aerosolized medication particles into the breathing circuit (e.g., via a nebulizer) for delivery to the patient's lungs. However, where an HME unit is present in the breathing circuit, the medication particles will not readily traverse the HM media and thus not be delivered to the patient.

In addition, the HM media can become clogged with the droplets of liquid medication, in some instances leading to an elevated resistance of the HME unit. One approach for addressing these concerns is to remove the HME unit from the breathing circuit when introducing aerosolized medication. This step is time consuming, subject to errors and can result in the loss of recruited lung volume when the circuit is depressurized.

Alternatively, various HME units have been suggested that incorporate intricate bypass structures/valves that selectively and completely isolate the HM media from the airflow path. For example, existing bypass-type HME units employ a bypass structure that is internal or through the HM media. While viable, these and other bypass-type HME units are difficult to operate (e.g., requiring a caregiver to rotate two frictionally fitting housing units relatively to each other) and/or are relatively complex and thus expensive.

In light of the above, a need exists for improved HME units having an HM media bypass feature that addresses one or more of the problems associated with conventional bypass-type HME units.

SUMMARY

Some aspects of the present disclosure relate to a heat and moisture exchange unit for use with a patient breathing circuit. The unit includes a housing, an MDI port assembly and a heat and moisture medium. The housing forms a patient-side port, a ventilator-side port, and a containment region between the patient-side port and the ventilator-side port. The MDI port assembly includes a frame projecting into the containment region and configured to receive a portion of a metered dose dispenser. The frame terminates at an outlet end, forming a flow passage. The heat and moisturizing medium is maintained within the containment region to define a medium face most proximate the outlet end of the MDI port assembly. The unit is characterized by the absence of a body between the outlet end and the medium face in some embodiments. In some embodiments, the heat and moisture exchange unit is characterized by an absence of a bypass pathway between the outlet end and the medium. In some embodiments, the heat and moisture exchange unit is characterized by an absence of a physical barrier between the outlet end and the medium.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present disclosure. The following detailed description, therefore, is not to be taken in a limiting sense, and the scope of the present disclosure is defined by the appended claims.

Figure 1:
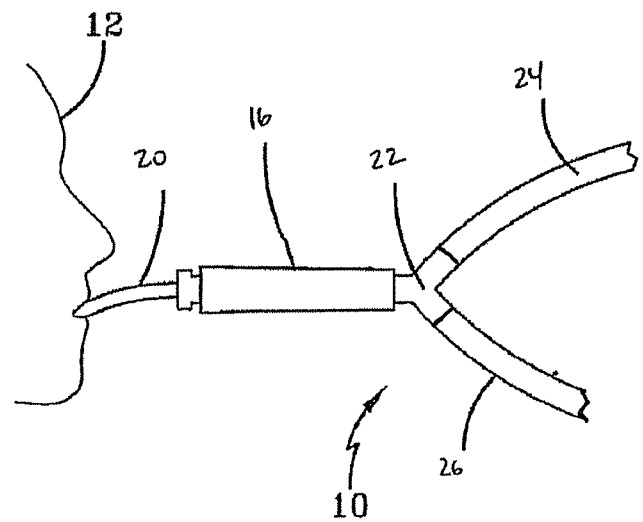
FIG. 1 is a simplified illustration of an example patient breathing circuit with which an HME unit in accordance with principles of the present disclosure is useful.

As illustrated in detail below, aspects in accordance with principles of the invention relate to an HME unit or apparatus useful with a patient breathing circuit. As a point of reference, FIG. 1 illustrates one such breathing circuit 10 as including a number of flexible tubing segments that are connected in between a patient 12 and a ventilator (not shown). The breathing circuit 10 of FIG. 1 is a dual limb breathing circuit, and can include a source of pressurized air 14, an HME unit 16 (shown in block form) in accordance with the present disclosure, and a nebulizer 18.

With the one non-limiting example of the breathing circuit 10 in mind, a patient tube 20 is provided that connects the patient 12 to the HME unit 16. An end of the patient tube 20 that interfaces with the patient 12 can be an endotracheal tube that extends through the patient's mouth and throat and into the patient's lungs. Alternatively, it also may be connected to a tracheostomy tube (not shown in FIG. 1, but referenced at 46 in FIG. 2) that provides air to the patient's throat and thereby to the patient's lungs.

Extending on an opposite side of the HME unit 16 is a connector 22, for example a Y-connector. The Y-connector 22 can be connected to additional tubing; for example, an exhalation tube 24 (commonly referred to as the "exhalation limb") that allows exhaled air to leave the breathing circuit 10. A second tube 26 (commonly referred to as the "inhalation limb") is connected to a ventilator (not shown).

Figure 2:
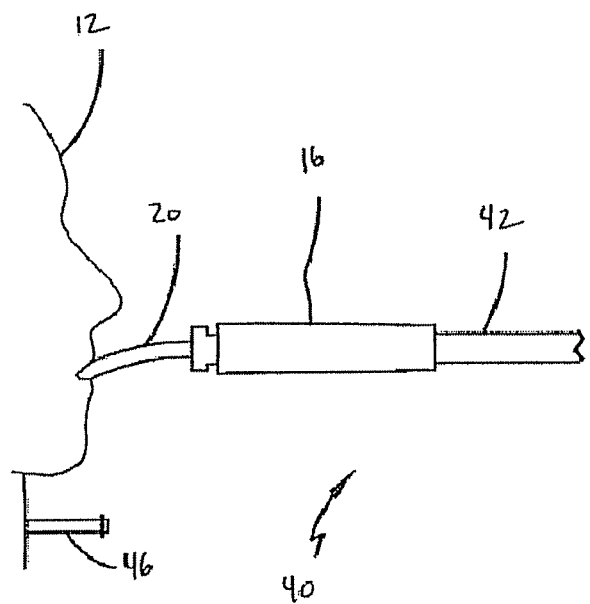
FIG. 2 is a simplified illustration of another example breathing circuit with which the HME unit in accordance with principles of the present disclosure is useful.
Figure 3:
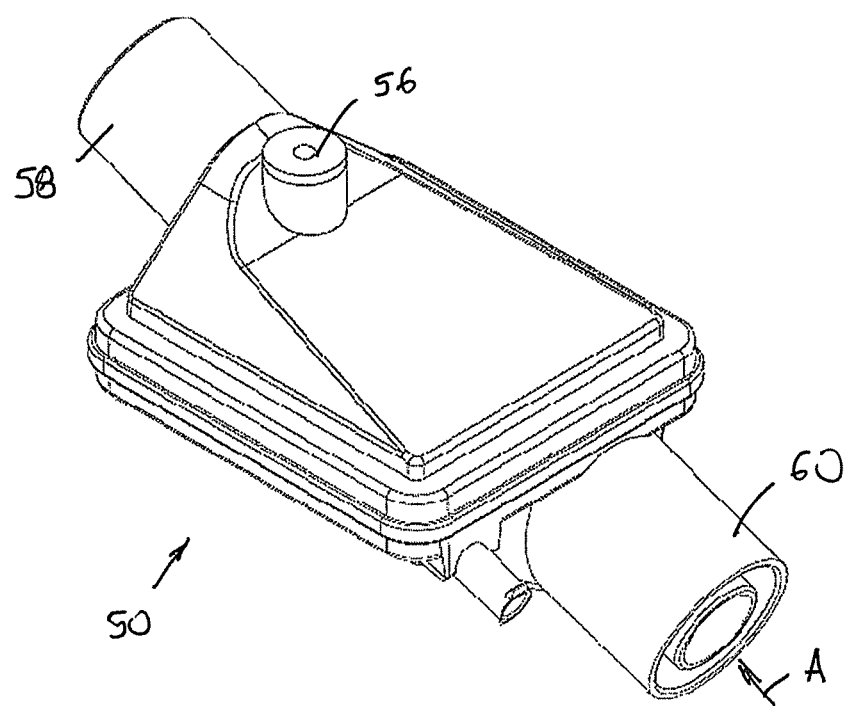
FIG. 3 is a perspective view of an HME unit for use in conjunction with an embodiment of the present disclosure.
Figure 4:
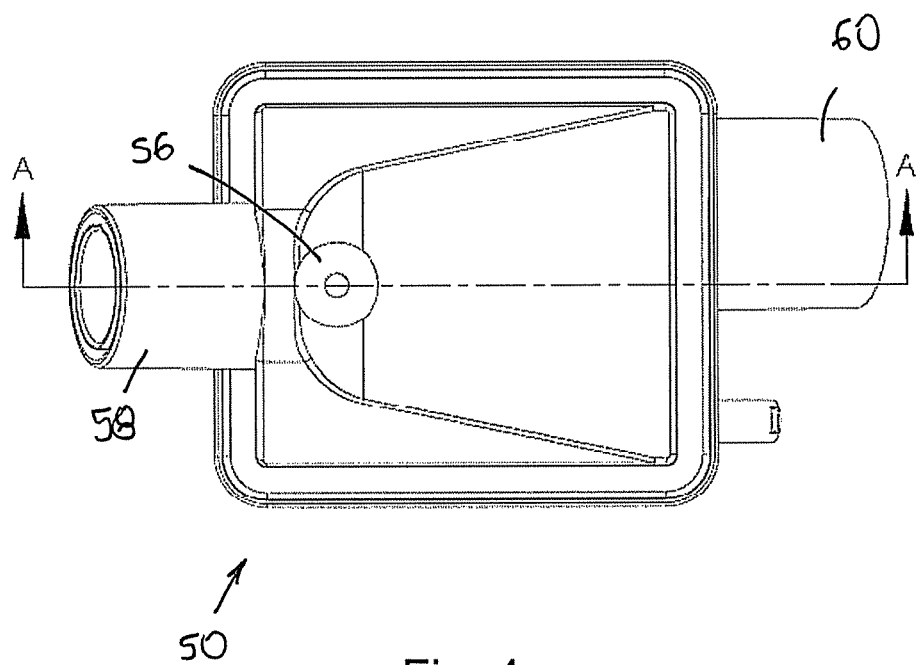
FIG. 4 is a top view of the HME unit.
Figure 5:
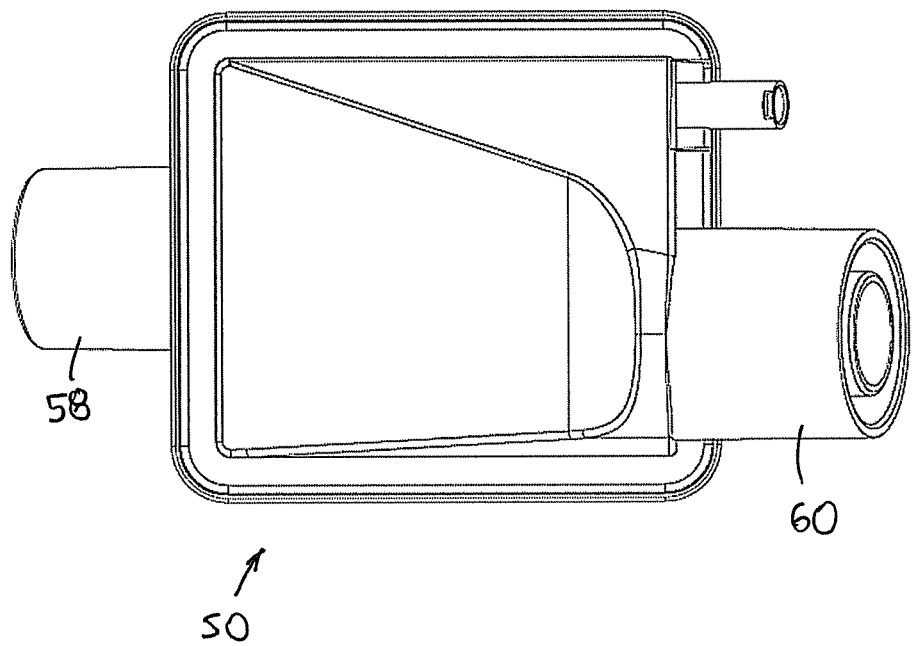
FIG. 5 is a bottom view of the HME unit.
Figure 6:
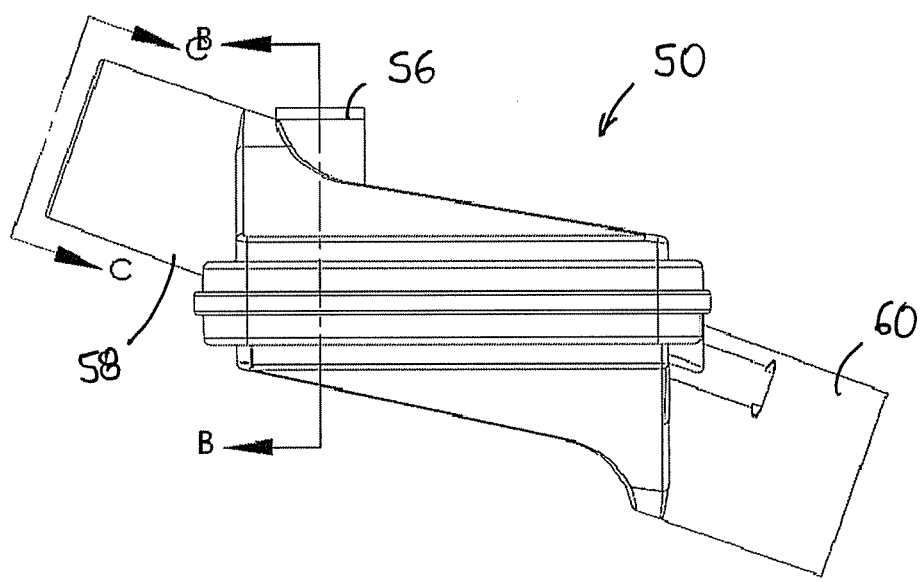
FIG. 6 is a side view of the HME unit.
Figure 7:
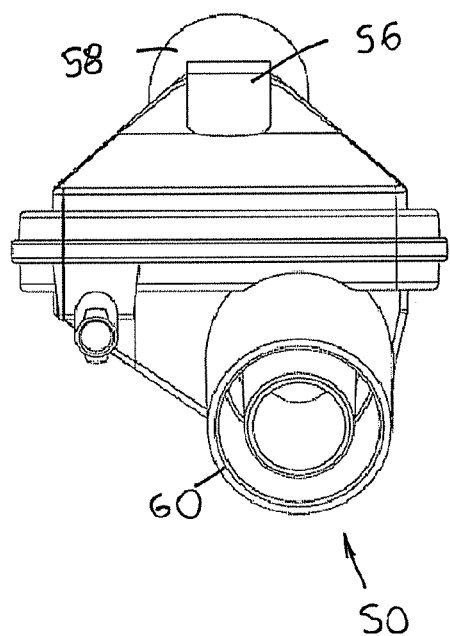
FIG. 7 is a first end view of the HME unit.
Figure 8:
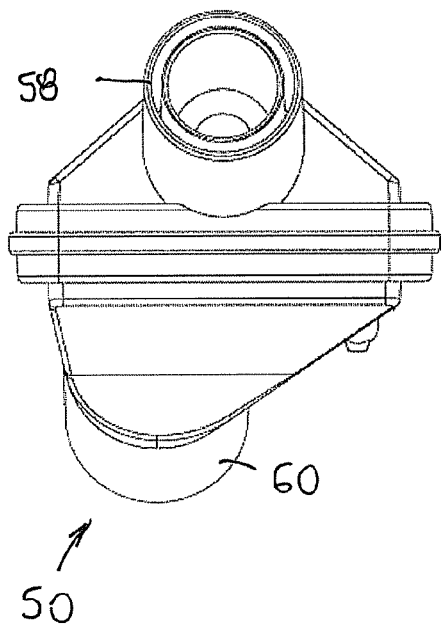
FIG. 8 is a second end view of the HME unit.

By way of further reference, FIG. 2 illustrates an alternative breathing circuit 40 with which the HME unit 16 of the present disclosure is useful. The breathing circuit 40 is a single limb breathing circuit that again serves to fluidly connect a ventilator (not shown) with the patient 12.

With the single limb breathing circuit 40, the patient tube 20 fluidly connects the patient 12 and the HME unit 16. A single tube 42 extends from the HME unit 16 opposite the patient 12. The ventilator (not shown) is directly connected to the HME unit 16 via a tube 42. When desired, the single limb breathing circuit 40 (as well as the dual limb breathing circuit 10 of FIG. 1) can be connected to a tracheostomy tube 46.

With the above general explanation of breathing circuits in mind, one configuration of an HME unit 50 useful as the HME unit 16 (FIGS. 1 and 2) is illustrated in FIGS. 3-11. The HME unit 50 includes a housing 52, a heat and moisture media (HM media) 54 and an MDI port 56. Details on the various components are provided below. In general terms, however, the housing 52 includes a first port 58, a second port 60 and an intermediate section 62.

The HM media 54 is sized and shaped for placement within a containment region of the intermediate section 62. In this regard, the HM media 54 can assume a variety of forms known in the art that provide heat and moisture retention characteristics, and typically is or includes a foam material. Other configurations are also acceptable, such as paper or filler-type bodies. In more general terms, then, the HM media 54 can be any material capable of retaining heat and moisture regardless of whether such material is employed for other functions such as filtering particles.

With some constructions, the HM media 54 has a generally rectangular shape, defining opposing, first and second major surfaces 70, 72. Upon final assembly, the HM media 54 is arranged such that the first major surface 70 fluidly faces the first port 58, whereas the second major face 72 fluidly faces the second port 60.

The configuration of the HME unit 50 may facilitate detaching the first port 58 from the second port 60 to replace the HM media 54. Alternatively, the HME unit 50 may be configured such that the entire unit is replaced if the HM media 54 becomes fouled or otherwise unusable.

Figure 9:
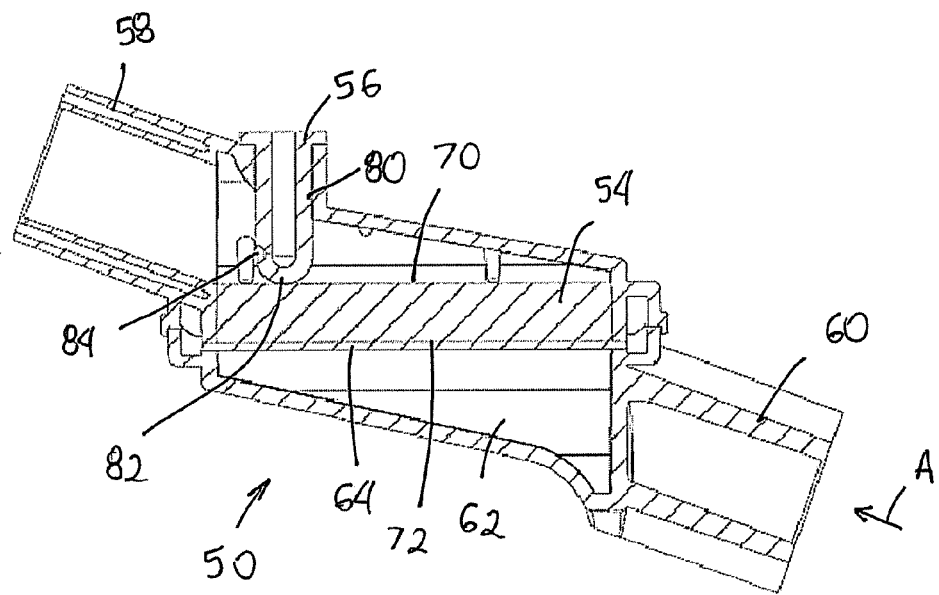
FIG. 9 is a sectional view of the HME unit taken along a line A-A in FIG. 4.

As illustrated in FIG. 9, the HM unit 50 thereby orients the HM media 54 such that a relatively large HM media surface area (i.e., the first or second major surface 70, 72) is presented within a first flow path A, yet overt airflow restrictions are minimized. More particularly, flow along the first airflow path A progresses through a thickness of the HM media 54, where the thickness may be less than a length or width of the HM media 54. As such, resistance to normal patient breathing through the HME unit 50 is minimized.

An optional filter 64 may be included with the HME unit 50 to remove particles that may foul or otherwise decrease the performance or life span of the HM media 54. The filter 64 may be positioned in the containment region 62 adjacent the second major face 72 such that the filter 64 is fluidly open to the ventilator-side port. As a point of reference, with embodiments in which the HME unit 50 does not include the optional filter 64, the containment region 62 can have a volume of not more than 30 mL in some embodiments; alternatively, with constructions including the filter 64, the containment region 62 can have a volume of not more than 60 mL.

Figure 10:
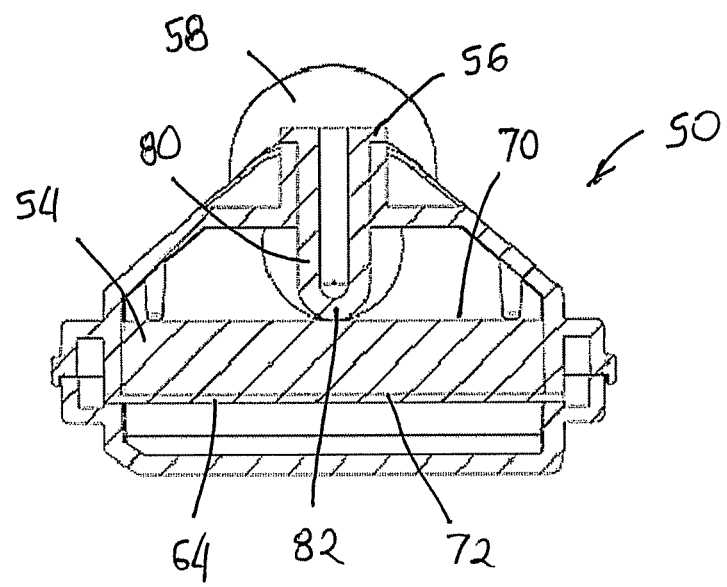
FIG. 10 is sectional view of the HME unit taken along a line B-B in FIG. 6.
Figure 11:
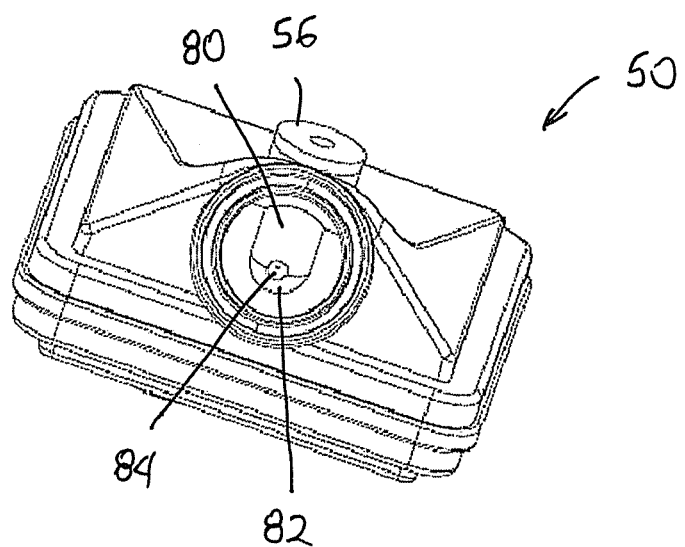
FIG. 11 is an angled end view of the HME unit taken along a line C-C in FIG. 6.

The MDI port assembly 56 includes a frame 80 that projects into the containment region 62, as illustrated in FIGS. 9-11. The MDI port assembly 56 is adapted to receive a portion of a metered dose dispenser (not shown). The frame terminates at an outlet end 82, forming a flow passage 84. The size and shape of the flow passage 84 may be varied, depending on the material being dosed through the MDI port assembly 56. The outlet end 82 is between the first port 58 and the first major surface 70. A distance between the outlet end 82 and the medium face 70 is not greater than about 0.5 inches.

When it is not desired to use the nebulizer 14, it is possible to disconnect the nebulizer 14 from the MDI port 56 and then insert a plug (not shown) into the MDI port 56 to thereby enable the patient breathing circuit 10, 40 to be pressurized as well as to prevent pathogens or other objects from entering the breathing circuit 10, 40.

The HME unit 50 may also include a resistance indicator (not shown). The resistance indicator can assume a variety of forms, and generally serves to identify instances where a differential pressure or resistance across the HME unit 50 has exceeded a predetermined value.

The resistance indicator is in fluid communication with the second port 60 along the first flow path A, and is thus exposed to an internal pressure differential within the HME unit 50 across the HM media 54. The resistance indicator can be mechanical (e.g., silicone diaphragm) and/or incorporate electronic components.

When triggered (i.e., in the presence of an excessive pressure differential across the HM media 54), the resistance indicator provides a warning or other indication to a caregiver of a potentially problematic state of the HME unit 50 (e.g., the HM media 54 is overly resisting airflow).

In this regard, where the resistance indicator is internally disposed within the housing 52, one or more exterior walls associated with the housing 52 and located in close proximity to the resistance indicator can be at least partially transparent such that the resistance indicator is viewable through the housing 52.

During use, the HME unit 50 is fluidly connected to a patient breathing circuit; for example, the breathing circuit 10 of FIG. 1 or the breathing circuit 40 of FIG. 2. The patient tube 20 is fluidly connected to the first port 58, and the second port 60 is fluidly connected to tubing connected to the ventilator (not shown). Thus, the first port 58 serves as a patient side port and the second port 60 serves as a ventilator side port.

Thus, airflow to and from the patient 12 via the HME unit 50 must pass through the HM media 54 (as well as the optional secondary filter 50 where provided), with the HM media 54 absorbing moisture and heat from exhaled air, and then transferring moisture and heat to the inhaled air provided to the patient's lungs.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A heat and moisture exchange unit for use with a patient breathing circuit, the unit comprising:
    a housing forming a patient-side port, a ventilator-side port, and a containment region between the patient-side port and the ventilator-side port;
    an MDI port assembly including a frame projecting into the containment region and configured to receive a portion of a metered dose dispenser, wherein the frame terminates at an outlet end forming a flow passage; and
    a heat and moisturizing medium defining opposing, first and second major exterior surfaces, wherein the medium is maintained within the containment region to locate the first major surface most proximate the outlet end of the MDI port assembly;
    wherein the unit is characterized by the absence of a body between the outlet end and the first major surface, and the unit is configured to establish a flow path from the ventilator-side port and constantly toward the patient-side port that enters the medium at the second major surface, exits the medium at the first major surface, passes along the outlet end of the MDI port assembly, and passes into the patient-side port.

2. The unit of claim 1, wherein the outlet end is fluidly between the first major surface and the patient-side port.

3. The unit of claim 1, wherein the first major surface is substantially entirely exposed relative to the outlet end.

4. The unit of claim 1 wherein the unit is characterized by the absence of a bypass pathway between the outlet end and the medium.

5. The unit of claim 1, wherein a distance between the outlet end and the first major surface is less than about 0.5 inches.

6. The unit of claim 1, wherein the housing includes a wall segment forming at least a portion of the containment region opposite the first major surface, and further wherein at least a portion of the MDI port assembly is integrally formed with the wall segment.

7. A patient breathing circuit for fluidly connecting a patient's airway with a supply of gas, the circuit comprising:
    a patient interface comprising:
        a first side configured to directly contact a patient's anatomy in fluidly connecting the patient interface to a patient's airway; and
        a second side opposite the first side, wherein the second side terminates at a patient interface outlet;
    a heat and moisture exchange unit comprising:
        a housing having a wall that forms a patient-side port, a ventilator-side port and a containment region between the patient-side port and the ventilator-side port, wherein the patient-side port is operably connected to the patient interface outlet;
        a heat and moisturizing medium maintained within the containment region;
        an MDI port configured to receive a portion of a metered dose dispenser and having an inlet end and an outlet end, wherein the MDI port extends through the wall;
        wherein the heat and moisture exchange unit is configured such that a direct linear flow path from the ventilator-side port to the patient-side port and intersecting the MDI port outlet end passes through a thickness of the medium; and
    tubing operably connected to the ventilator-side port for fluidly connecting the circuit to a source of gas.

8. The circuit of claim 7, wherein the containment region has a volume of not more than 30 mL.

9. The circuit of claim 7, wherein a distance between the outlet end of the MDI port and the medium is less than about 0.5 inches.

10. The circuit of claim 7, wherein the outlet end of the MDI port is fluidly between the medium and the patient-side port.

11. The circuit of claim 7, wherein the exchange unit is characterized by the absence of a physical barrier between the outlet end of the MDI port and the medium.

12. A heat and moisture exchange unit for use with a patient breathing circuit, the unit comprising:
    a housing having a wall that forms a patient-side port, a ventilator-side port and a containment region between the patient-side port and the ventilator-side port;
    a heat and moisturizing medium having opposed, first and second major surfaces, wherein the medium is maintained within the containment region such that the first major surface is fluidly open to the patient-side port;
    a filter maintained within the containment region and positioned adjacent the second major surface of the medium such that the filter is fluidly open to the ventilator-side port; and
    an MDI port configured to receive a portion of a metered dose dispenser and having an inlet end and an outlet end, wherein the MDI port extends through the wall of the housing along the containment region such that the outlet end is most proximate the first major surface of the medium;
    wherein the unit is configured to establish a flow path from the ventilator-side port and constantly toward the patient-side port that passes through the filter, through the medium, along the MDI port outlet end, and into the patient side port.

13. The unit of claim 12, wherein the containment region has a volume of not more than 60 mL.

14. The unit of claim 12, wherein apart from the housing, the first major surface of the medium is substantially entirely exposed.

15. The unit of claim 12, wherein the outlet end of the MDI port defines an opening through which fluid from a dispenser received within the MDI port is projected into the housing, wherein the opening defines an axis intersecting the patient-side port.

16. The unit of claim 12, wherein a distance between the outlet end and the first major surface of the medium is less than 0.5 inch.

17. The unit of claim 12, wherein the housing includes a wall segment forming at least a portion of the containment region opposite the first major surface of the medium, and wherein at least a portion of the MDI port is integrally formed with the wall segment.

18. The unit of claim 12, wherein a distance between the patient-side port and the first major surface of the medium is less than 0.5 inch.

* * * * *